(12) United States Patent
Forsyth et al.

(10) Patent No.: US 11,154,197 B2
(45) Date of Patent: Oct. 26, 2021

(54) INFLATABLE MEMBRANE FOR FLUORESCENT IMAGING AND IMPROVEMENTS IN DYE MATERIALS

(71) Applicant: Lantos Technologies, Inc., Cambridge, MA (US)

(72) Inventors: Alison M. Forsyth, Boston, MA (US); Manas Menon, Boston, MA (US); Stan Najmr, Cambridge, MA (US); Federico Frigerio, Chestnut Hill, MA (US); Ben Frantzdale, Shrewsbury, MA (US); Michael Rishton, Cambridge, MA (US)

(73) Assignee: LANTOS TECHNOLOGIES, INC., Derry, NH (US)

(*) Notice: Subject to any disclaimer, the term of this patent is extended or adjusted under 35 U.S.C. 154(b) by 1021 days.

(21) Appl. No.: 14/214,396

(22) Filed: Mar. 14, 2014

(65) Prior Publication Data

US 2014/0272221 A1    Sep. 18, 2014

Related U.S. Application Data

(60) Provisional application No. 61/790,491, filed on Mar. 15, 2013.

(51) Int. Cl.
*A61B 5/00* (2006.01)
*A61B 1/227* (2006.01)
(Continued)

(52) U.S. Cl.
CPC ............ *A61B 5/0071* (2013.01); *A61B 1/227* (2013.01); *A61B 5/0064* (2013.01);
(Continued)

(58) Field of Classification Search
CPC ... A61B 5/0071; A61B 5/0064; A61B 5/0062; A61B 5/0084; A61B 1/227;
(Continued)

(56) References Cited

U.S. PATENT DOCUMENTS 3,790,653 A * 2/1974 Barkey at al. ........... C08K 3/04
264/210.5
4,643,733 A * 2/1987 Becker .................. A61B 90/02
128/899

(Continued)

FOREIGN PATENT DOCUMENTS

CA        2840602 A1    1/2013
JP        H08243262 A    9/1996
(Continued)

OTHER PUBLICATIONS

WelchAllyn CompacVideo Otoscope Model 23120 (NTSC) and 23120P (PAP), Operating Instruction Manual, 2000, 16 pages.
(Continued)

*Primary Examiner* — James C Yager
(74) *Attorney, Agent, or Firm* — GTC Law Group PC & Affiliates (57) ABSTRACT

An inflatable membrane for use with a three-dimensional (3D) scanning system configured to measure signal intensity of a first and a second wavelength of light may include a matrix material, a pigment for opacity, and a fluorescent material that is transparent to the first and the second wavelengths of light. The first and second wavelengths of light may be ranges of wavelengths. The matrix material may include a silicone, and the pigment for opacity may include a carbon black. The 3D scanning system may be configured to scan anatomical cavities, such as the human ear canal.

17 Claims, 9 Drawing Sheets

(51) Int. Cl.
*C08K 3/04* (2006.01)
*A61B 5/107* (2006.01)

(52) U.S. Cl.
CPC .......... *A61B 5/0084* (2013.01); *A61B 5/6817* (2013.01); *A61B 5/1076* (2013.01); *A61B 5/4887* (2013.01); *C08K 3/04* (2013.01); *Y10T 428/1345* (2015.01)

(58) Field of Classification Search
CPC ..... A61B 5/6817; A61B 5/064; A61B 5/1076; A61B 5/4887; Y10T 428/1345; C08K 3/04
See application file for complete search history.

(56) References Cited

U.S. PATENT DOCUMENTS

| | | |
|---|---|---|
| 5,100,587 A * | 3/1992 | Clough .................. C09K 11/04 252/301.17 |
| 5,504,316 A | 4/1996 | Bridgelall et al. |
| 5,829,350 A | 11/1998 | Muchi et al. |
| 6,001,059 A | 12/1999 | Elliott |
| 8,032,337 B2 | 10/2011 | Deichmann et al. |
| 8,047,207 B2 | 11/2011 | Perez et al. |
| 8,107,086 B2 | 1/2012 | Marini et al. |
| 8,384,916 B2 | 2/2013 | Hart et al. |
| 8,840,566 B2 | 9/2014 | Seibel et al. |
| 8,845,526 B2 | 9/2014 | Hart et al. |
| 9,291,565 B2 | 3/2016 | Hart et al. |
| 10,122,989 B2 | 11/2018 | Fei et al. |
| 2003/0164952 A1 | 9/2003 | Deichmann et al. |
| 2005/0191451 A1* | 9/2005 | Osika .................... B29C 49/221 428/35.7 |
| 2007/0106012 A1* | 5/2007 | Matyjaszewski ......... C08F 2/38 524/555 |
| 2008/0027358 A1 | 1/2008 | Gregersen et al. |
| 2008/0058629 A1 | 3/2008 | Seibel et al. |
| 2009/0289938 A1 | 11/2009 | Paulsen |
| 2010/0019170 A1 | 1/2010 | Hart et al. |
| 2010/0039534 A1 | 2/2010 | Hart et al. |
| 2010/0042002 A1 | 2/2010 | Hart et al. |
| 2010/0296664 A1 | 11/2010 | Burgett et al. |
| 2011/0009702 A1 | 1/2011 | Morishita et al. |
| 2011/0076608 A1* | 3/2011 | Bergemann ............... C09C 1/56 430/108.9 |
| 2011/0290005 A1* | 12/2011 | Hart ................... G01B 11/0658 73/37.9 |
| 2012/0327426 A1 | 12/2012 | Hart et al. |
| 2013/0002824 A1 | 1/2013 | Hart et al. |
| 2013/0027516 A1 | 1/2013 | Hart et al. |
| 2013/0078555 A1 | 3/2013 | Orihara et al. |
| 2013/0261655 A1 | 10/2013 | Drasler et al. |
| 2014/0275974 A1 | 9/2014 | Samuels |
| 2014/0276005 A1 | 9/2014 | Forsyth et al. |
| 2014/0276105 A1 | 9/2014 | De Brouchoven et al. |
| 2014/0330133 A1 | 11/2014 | Stern |
| 2015/0036146 A1 | 2/2015 | Staloff |
| 2016/0150949 A1 | 6/2016 | Patterson et al. |
| 2017/0104977 A1 | 4/2017 | Fei et al. |
| 2018/0178419 A1 | 6/2018 | Fei et al. |
| 2018/0319047 A1 | 11/2018 | Fei et al. |
| 2019/0014309 A1 | 1/2019 | Fei et al. |

FOREIGN PATENT DOCUMENTS

| | | |
|---|---|---|
| WO | WO-2012115863 A2 | 8/2012 |
| WO | WO-2013003416 A2 | 1/2013 |
| WO | 2014145026 A2 | 9/2014 |
| WO | 2014145058 A1 | 9/2014 |
| WO | 2014145077 A1 | 9/2014 |
| WO | 2015017779 A1 | 2/2015 |
| WO | 2016086005 A1 | 6/2016 |
| WO | 2017062868 A1 | 4/2017 |
| WO | 2017062868 A8 | 4/2017 |
| WO | 2018118772 A9 | 6/2018 |

OTHER PUBLICATIONS

U.S. Appl. No. 14/214,406, filed Mar. 14, 2014.
U.S. Appl. No. 14/214,414, filed Mar. 14, 2014.
International Search Report and Written Opinion dated Jul. 31, 2014 for PCT application No. PCT/US2014/029712.
International Search Report and Written Opinion dated Aug. 7, 2014 for PCT application No. PCT/US2014/029738.
International Search Report and Written Opinion dated Sep. 11, 2014 for PCT application No. PCT/US2014/029662.
Park, "3D scan designs headphones just for you", [retrieved Dec. 19, 2016], http://www.unitedsciences.com/151-2, Jan. 10, 2015, 2 pages.
PCT/US15/62464, "International Application Serial No. PCT/US15/62464, International Preliminary Report on Patentability, dated May 30, 2017", Lantos Technologies Inc., 5 pages.
PCT/US15/62464, "International Application Serial No. PCT/US15/62464, International Search Report and Written Opinion dated Mar. 31, 2016", Lantos Technologies Inc., 7 pages.
PCT/US16/56132, "International Application Serial No. PCT/US16/56132, International Preliminary Report on Patentability and Written Opinion dated Apr. 19, 2018", Lantos Technologies Inc., 7 Pages.
PCT/US16/56132, "International Application Serial No. PCT/US16/56132, International Search Report and Written Opinion dated Jan. 26, 2017", Lantos Technologies, Inc., 8 pages.
PCT/US17/67010, "International Application Serial No. PCT/US17/67010, International Search Report and the Written Opinion dated Mar. 9, 2018.", Lantos Technologies Inc., 11 pages.
PCT/US2014/029662, "International Application Serial No. PCT/US2014/029662, International Preliminary Report on Patentability dated Sep. 24, 2015", 5 pages.
PCT/US2014/029712, "International Application Serial No. PCT/US2014/029712, International Preliminary Report on Patentability dated Sep. 24, 2015", 5 pages.
PCT/US2014/029738, "International Application Serial No. PCT/US2014/029738 International Preliminary Report on Patentability dated Sep. 24, 2015", 5 pages.

* cited by examiner

INFLATABLE MEMBRANE FOR FLUORESCENT IMAGING AND IMPROVEMENTS IN DYE MATERIALS

CROSS-REFERENCE TO RELATED APPLICATION

This application claims priority to U.S. Provisional Patent Application Ser. No. 61/790,491, titled "Apparatus and Methods for Probing and Measuring Anatomical Cavities," filed Mar. 15, 2013, the disclosure of which is hereby incorporated by reference herein.

FIELD

The subject matter described herein relates to inflatable membranes used in probing and measuring cavities, particularly anatomical cavities such as a human ear canal.

BACKGROUND

Devices can be created to fit into anatomical cavities, such as the human ear canal. When creating such devices, having a comfortable and snug fit between a device and the cavity into which it is placed can increase the likelihood that a user will wear the device, as well as enhance the performance of the device.

Traditional methods of probing and measuring sensitive cavities, such as anatomical cavities, include creating impressions of the cavity. Creating or taking an impression includes injecting a material into the cavity. The material is allowed to harden and conform to the shape of the cavity, and then the material is extracted from the cavity. An impression created this way can cause complications or pain when the impression material is injected into the cavity, when the material is hardening, and/or when the impression is extracted. Such actions can exert pressure on the walls of the cavity in a painful or damaging way.

SUMMARY

Methods, systems, and apparatus, including computer program products, are provided for scanning systems including inflatable membranes for probing and measuring anatomical cavities. For some example implementations, there is provided an inflatable membrane for use with a three-dimensional scanning system. The membrane includes a matrix material, a pigment for opacity, and a fluorescent material.

In some implementations, the above-noted aspects of an inflatable membrane for use with a three-dimensional scanning system may further include additional features described herein including one or more of the following. The matrix material may include silicone in some implementations of the inflatable membrane. In some implementations, the pigment for opacity includes a carbon black. In such implementations, the carbon black may include furnace carbon black. The furnace carbon black in some implementations of the inflatable membrane may be high-purity carbon black. The carbon black may include at least one of: total polynuclear aromatic hydrocarbons at a level not exceeding about 0.5 parts per million; and benzo[a]pyrene at a level not exceeding about 5.0 parts per billion. The carbon black may include primary particles with diameters ranging from about 15 nm to about 20 nm. In some implementations of an inflatable membrane, the fluorescent material may include a material with a high Stokes' shift. In some implementations, the fluorescent material may be excited by light with wavelengths ranging from ultra-violet to blue light. The fluorescent material may have emission spectra with a peak at a wavelength of about 549 nanometers. In some implementations, the fluorescent material may include a fluorescent dye. Alternatively, or additionally, the fluorescent material may include a fluorescent pigment.

For some example implementations, there is provided a method of creating a fluorescent inflatable membrane material. The method may include measuring a predetermined weight of a matrix material, a pigment for opacity, and a fluorescent material; and placing the matrix material, the pigment for opacity, and the fluorescent material in a mixing container. The method may also include mixing the matrix material, the pigment for opacity, and the fluorescent material in the mixing container according to a protocol to produce a masterbatch mixture. The method may then include mixing the masterbatch mixture with an additional portion of the matrix material to create a spreadable membrane mixture, casting the spreadable membrane mixture, and curing the spreadable membrane mixture.

In some implementations, the above-noted aspects of a method of creating a fluorescent inflatable membrane material may further include additional features described herein including one or more of the following. In some implementations, the casting may include liquid injection molding, injection molding, compression molding, transfer molding, or any combination thereof. The pigment for opacity may include carbon black in some implementations. In some such implementations, the carbon black may include a high-purity furnace carbon black. In some implementations, the carbon black can include primary particles with diameters ranging from about 15 nm to about 20 nm. The fluorescent material used in the method may include a fluorescent pigment and/or dye with a high Stokes' shift.

The above-noted aspects and features may be implemented in systems, apparatus, methods, and/or articles depending on the desired configuration. The details of one or more variations of the subject matter described herein are set forth in the accompanying drawings and the description below. Features and advantages of the subject matter described herein will be apparent from the description and drawings, and from the claims.

Like labels are used to refer to same or similar items in the drawings.

DETAILED DESCRIPTION

Injection of materials into sensitive cavities, such as anatomical cavities, can, as noted, cause pain and/or damage to the cavity. Alternative methods for probing and measuring such cavities may include scanning techniques that utilize light. Described herein are methods, apparatus, and systems for scanning techniques for probing and measuring anatomical cavities, including the human ear canal.

Figure 1A:
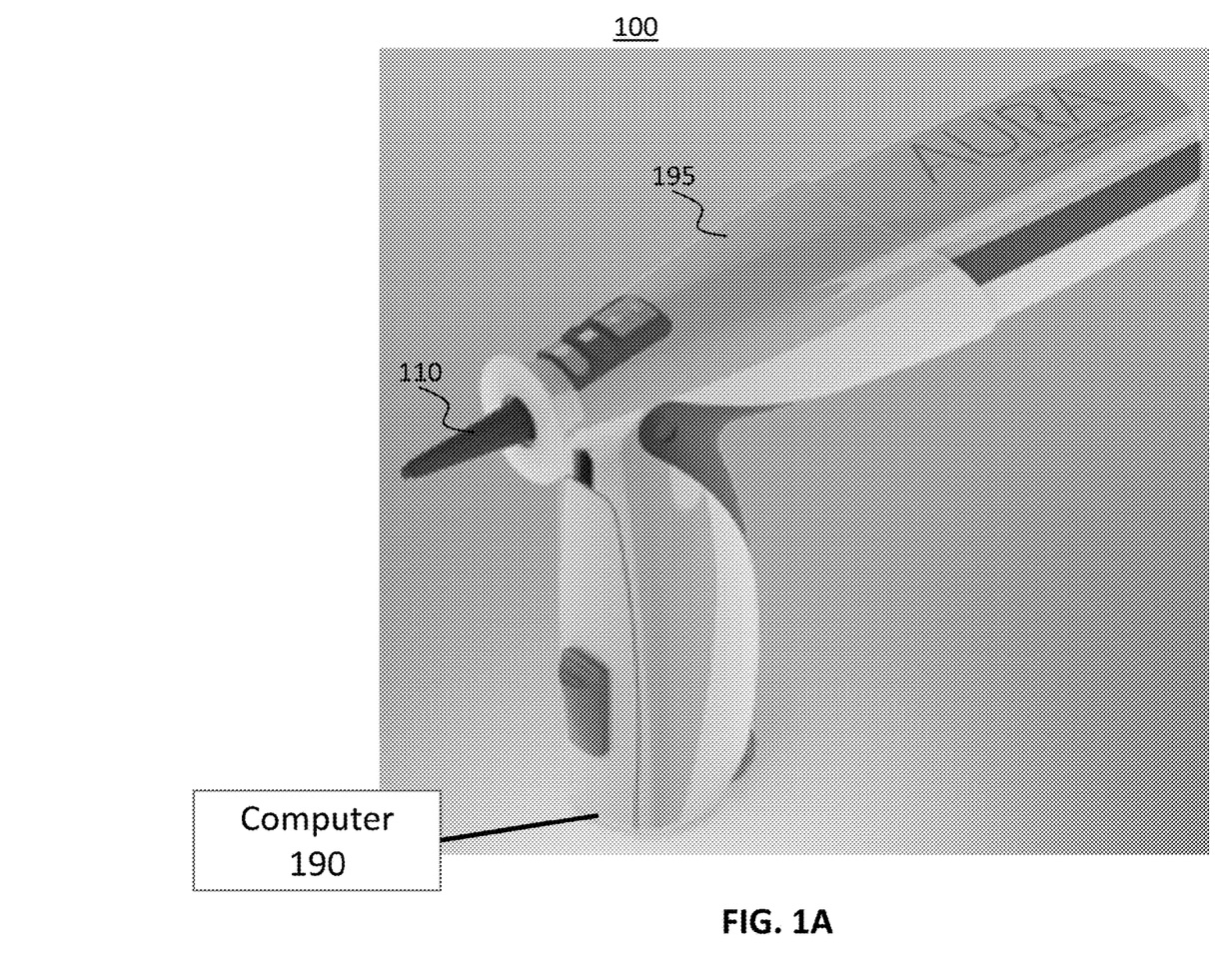
FIG. 1A depicts an example of a system including a three-dimensional (3D) scanner having an inflatable membrane.

FIG. 1A depicts a system 100 including an inflatable membrane 110, in accordance with some example implementations. The system 100 may generate three-dimensional (3D) scans of a cavity, such as an ear cavity.

Figure 1B:
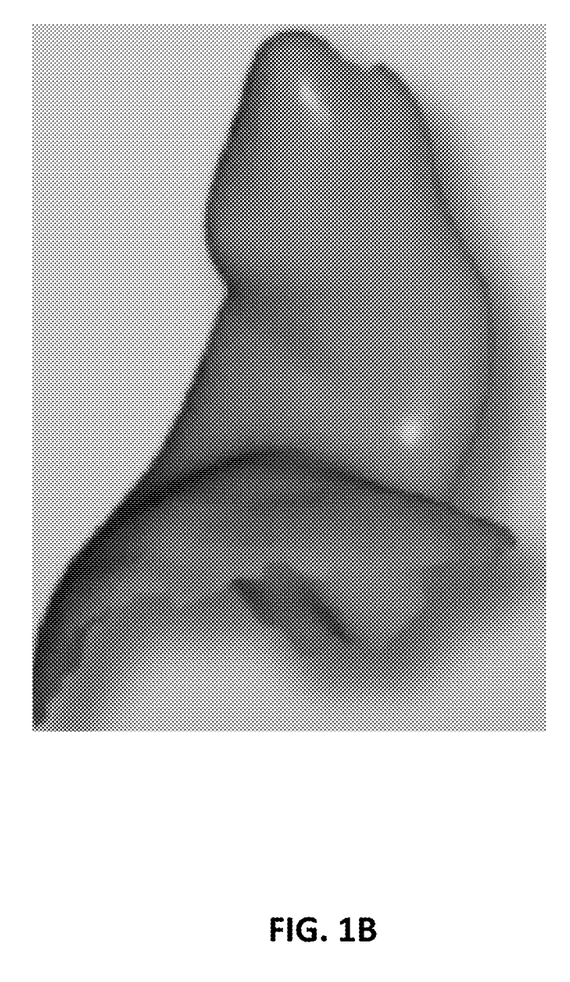
FIG. 1B depicts an example 3D rendering of a cavity formed based on scanner data collected by the 3D scanner of FIG. 1A.

System 100 may include a 3D scanner 195 including inflatable membrane 110 and a processor 190, such as computer. The processor 190 may process scanner data generated by 3D scanner 195 during a scan of the cavity. The processor 190 may form an output, such as a 3D impression of the scanned cavity. FIG. 1B depicts an example of a 3D surface formed by processor 190 based on scan data provided by 3D scanner 195. The 3D surface may model the cavity being scanned, such as an ear cavity, and this 3D surface may be provided to a manufacturer, 3D printer, and the like to form an object. In the case of the ear, the object may be an earpiece.

Figure 1C:
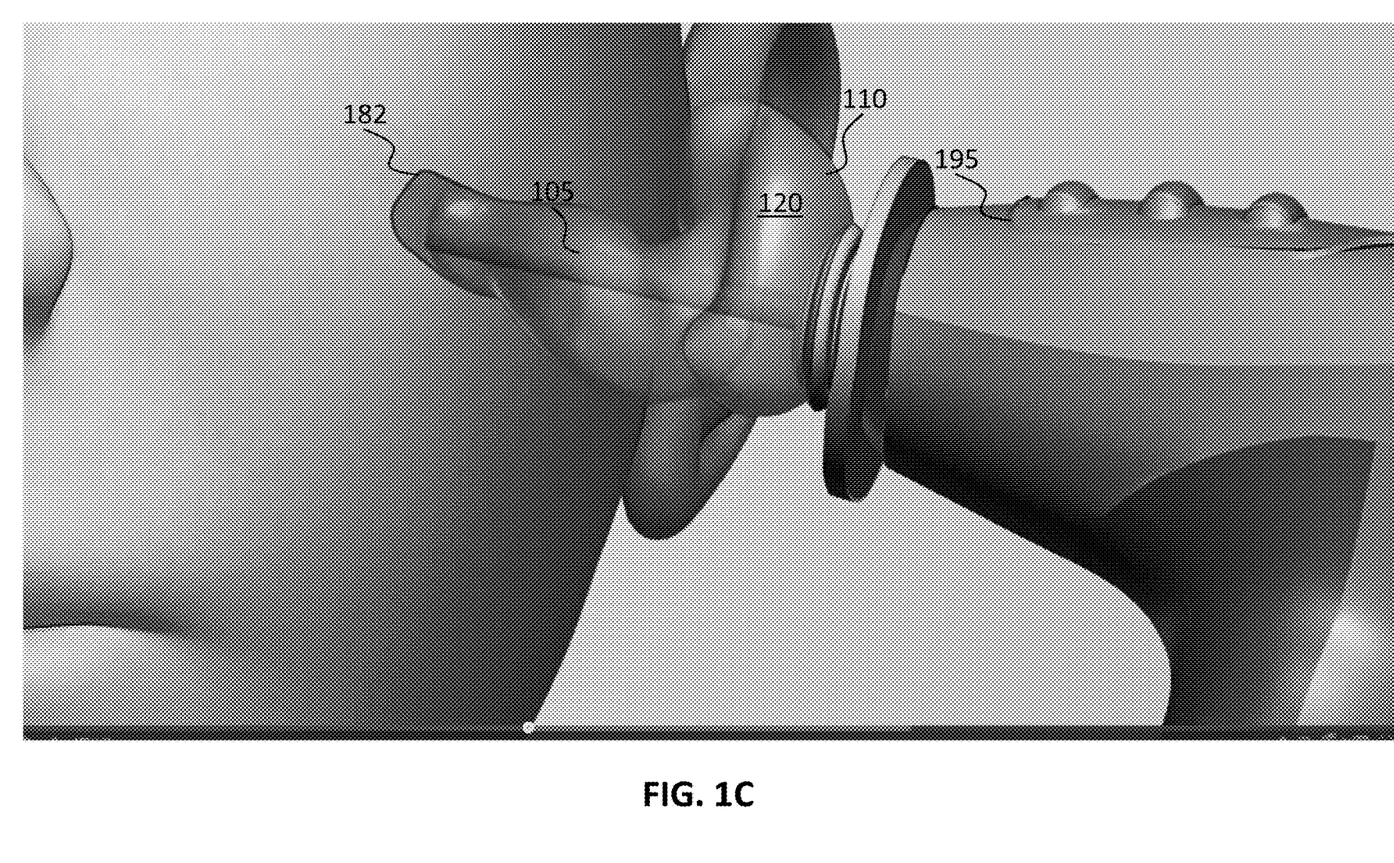
FIGS. 1C-D depict examples of a system including a 3D scanner having an inflatable membrane.

FIG. 1C depicts a portion of 3D scanner 195 after being inserted into an ear cavity 182 and after a medium 120 is used to expand interior of the inflatable membrane 110, so that the inflatable membrane 110 conforms to the ear cavity 182 (or portion of the ear cavity and/or any other cavity or surface being scanned). For example, the medium 120 may be inserted into the membrane 110, so that membrane 110 conforms to the cavity being scanned. At this point, scanner element 105 may scan the interior surface of the inflatable membrane 110 which when inflated with the medium 120 conforms to the ear cavity 182. The scanner element 105 may move within the membrane 110 to scan the interior surface of membrane 110. In this way, scanner element 105 may scan the interior surface of the membrane 110 and thus ear cavity 182. The scanner element 105 may generate a 2D image of the inflatable membrane approximating a snap shot of the anatomical cavity. Each pixel of the 2D image is then associated with distance information obtained during a scan, that is the distance from the scanner element 105 to the scanned portion of the membrane. The combination of the 2D image and distance information for each pixel of the 2D image corresponds to 3D data (for example, a 3D surface representative of the scanned cavity). In some implementations, the distance information determined from scanning data can correlate to groups of pixels, instead of a single pixel, on the 2D image.

Medium 120 may be a liquid, a gas, a gel, a hydrogel, and/or any combination of the four. The medium 120 may include additives dissolved into, or suspended in, the medium 120 to provide properties, such as selective absorption where one or more wavelengths of light are absorbed more than one or more other wavelengths. To illustrate, medium 120 may include a colored dye, suspension, a luminescent substance, and/or a fluorescent substance (and/or any other material having selective wavelength properties). The medium may also contain a bio-neutralizing, anti-microbial, or anti-oxidizing agent to improve the shelf life of the medium as well as a buffering agent to improve the stability of the medium. Moreover, the selective wavelength properties may, as described further below, allow 3D scanner and/or processor 190 to determine the shape of, distance to, and/or other properties of the scanned interior surface of membrane 110.

The inflatable membrane 110 may be implemented as any viscoelastic, elastic, plastic, and/or any other material that may be inflated to conform to the cavity, when the membrane 110 is inserted and inflated with medium 120. When the cavity corresponds to an ear canal, membrane 110 may have an inflated 3D shape and size that is substantially adapted to the ear cavity, although the membrane 110 may be used with other cavities and forms as well including a stomach, an esophagus, a bladder, and so forth. The membrane 110 may also include, or be coated with, a material to make the membrane fluoresce in the presence of white light, light of a particular wavelength, or a range of wavelengths, as further described below. In some implementations, the inflatable membrane may have a balloon-like shape with an opening, an interior surface, and an exterior surface. In some implementations, scanning the interior membrane 110, rather than the ear cavity directly, may reduce (if not eliminate) the interference caused by artifacts, such as ear hair, wax, and the like, and may thus improve the quality of the cavity scan.

Figure 1D:
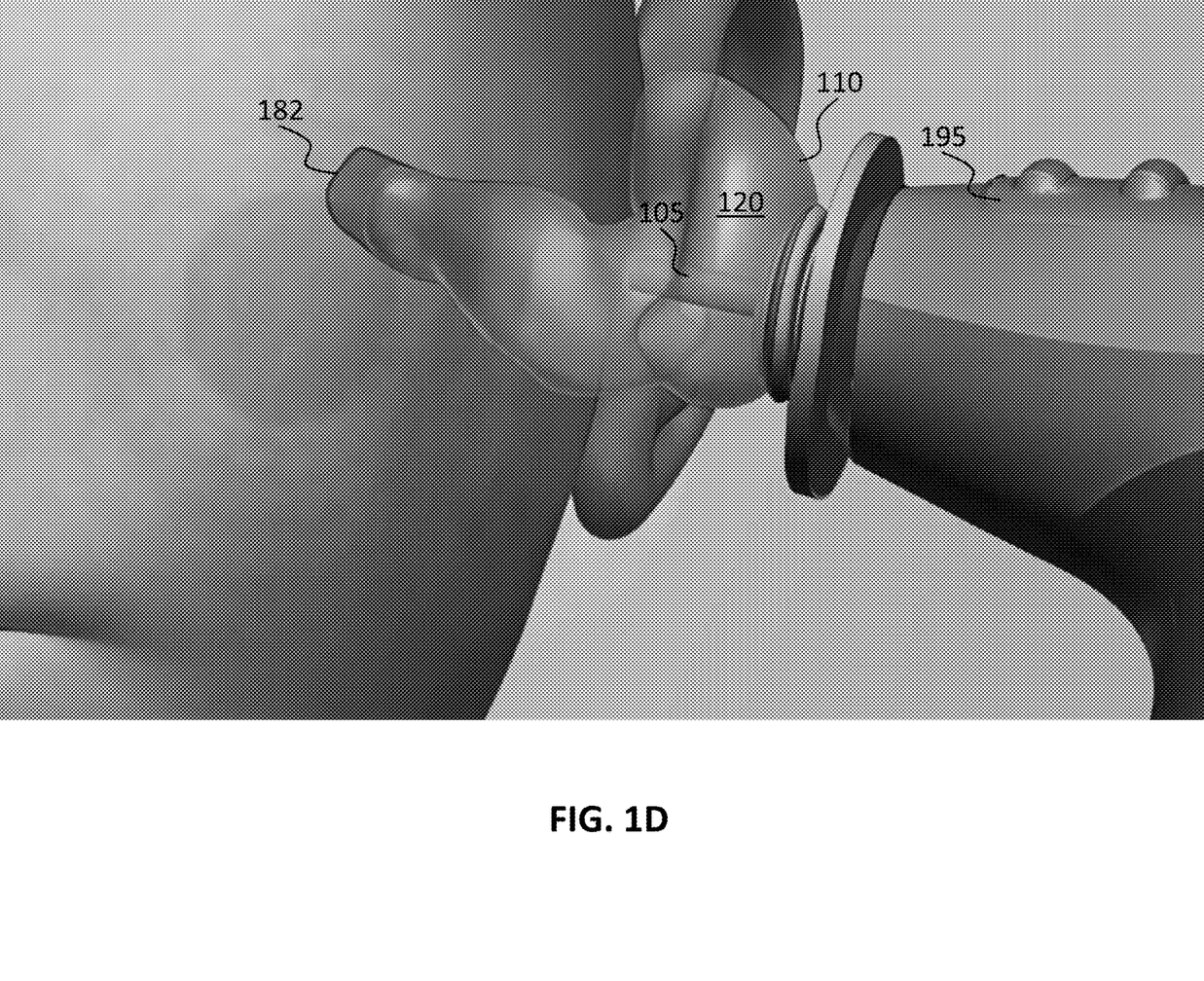

FIG. 1D depicts scanner element 105 after the scanner element has moved towards the opening of the cavity as part of the cavity scanning process. While scanning, scanner element 105 may scan one or more portions of the interior surface of the membrane 110, and element 105 may move within the membrane (and ear cavity 182) to image some (if not all) of the inner membrane 110/cavity 182. The scanner data collected by 3D scanner 195 may then be provided to one or more processors, such as computer 190 and/or a cradle-like device including an intermediary processor, to form a 3D surface or impression representative of the cavity as depicted at FIG. 1B, although some (if not all) of the processing may be performed by a processor contained in the 3D scanner 195 as well.

Figure 1E:
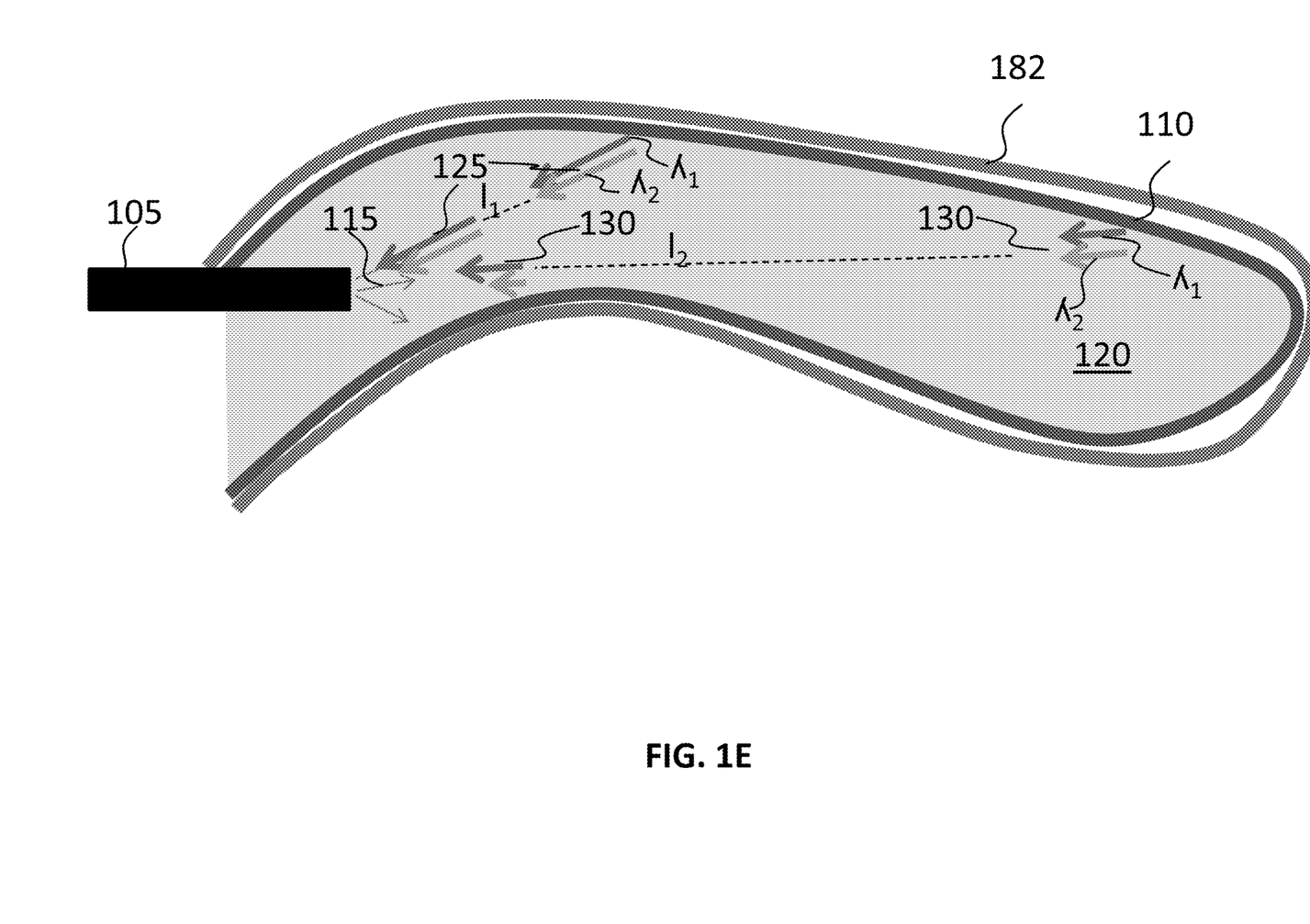
FIG. 1E shows a block diagram of a tip portion of the 3D scanner of FIGS. 1A, C, and D.

FIG. 1E shows a block diagram of the tip portion of 3D scanner 195 and, in particular, scanner element 105, inflatable membrane 110, and medium 120. The 3D scanner 195 and/or the scanner element 105 may include at least one light source, such as a light emitting diode, for emitting light 115 into the inflatable membrane 110, including medium 120. The scanner element 105 may also collect and/or detect light 125 and 130 that is emitted from fluorescent material in, or on, the inflatable membrane 110. The light 115 emanating from scanner element 105 may comprise light used to excite the fluorescent material in, or on, the inflatable membrane 110. Further, light from the fluorescent material in, or on, the inflatable membrane 110 may be referred to as "fluoresced" light, i.e., light resulting from the interaction of the fluorescent material with the light from scanner element 105.

The inflatable membrane 110 may include a fluorescent material, such as one or more fluorescent dyes, pigments, or other coloring agents. The fluorescent material can be homogenously dispersed within the inflatable membrane 110, although the fluorescent material may be applied in other ways as well (for example, the fluorescent material may be pad printed onto the surface of the inflatable membrane). The fluorescent material may be selected so that the fluorescent material is excited by one or more wavelengths of light 115 emitted by the scanner element 105. Once the fluorescent material is excited by light 115, the fluorescent material may emit light at two or more wavelengths $\lambda_1$, $\lambda_2$, or a range of wavelengths. For example, wavelength $\lambda_1$ may represent a range of wavelengths associated generally with red, although wavelength $\lambda_1$ may be associated with other parts of the spectrum as well.

As the two or more wavelengths 125 transmit back through the medium 120, medium 120 may absorb one or more of the wavelengths of light $\lambda_1$, $\lambda_2$ to a greater degree than one or more other wavelengths of the light. The medium 120 used in the system 100 may also be selected to optimally and preferentially absorb one or more of the wavelengths or a range of wavelengths of light from the fluorescent material of the inflatable membrane. By selecting an absorbing medium that complements the fluorescent material, the scan data collected by the 3D scanner may be more accurate.

When the tip portion 100 of 3D scanner 195 is inserted into ear cavity 182, 3D scanner 195 may pump (or insert in other ways) medium 120 into inflatable membrane 110 until the inflatable membrane 110 conforms to the surface of the cavity 182. Once the inflatable membrane 110 is fully inflated, 3D scanner and/or scanner element 105 may include a light emitting diode that generates light 115. Light 115 may travel from the scanner element 105, through medium 120, and excite the fluorescent material on, or in, a portion of the inflatable membrane 110. The light emitted from the fluorescent material on, or in, the inflatable membrane 110 may include at least two wavelengths of light. One of the wavelengths of light or some ranges of wavelengths of light emitted by the fluorescent material may be selectively absorbed by the medium 120. The light $\lambda_1$, $\lambda_2$ or ranges of light, may then be received by the scanner element 105, and the ratio of the intensities of light $\lambda_1$, $\lambda_2$ or the ratio of the integral area of light found under specific ranges may be measured and recorded by 3D scanner 195 and/or processor 190 to determine a distance from the scanner element 105 to corresponding surface of the membrane 110. The scanner element 105 may move throughout interior of membrane 110 to scan various portions of the surface of the membrane 110 and receive the fluoresced wavelength of light 125, 130 in order to collect data that can be used by the 3D scanner 195 and/or processor 190 to form 3D surface representative of the cavity. Alternatively, or additionally, the scanner element 105 may include optical, electronic, or mechanical means of focusing and directing the light used to excite the fluorescent material. Although the scanner element 105 may include one or more components, such as one or more light emitting diodes, optics, lenses, detectors/CCDs/CMOS sensors, and the like, one or more of these components may be located in other portions of the 3D scanner (for example, a fiber may carry light 115 to scanner element 105).

Figure 1F:
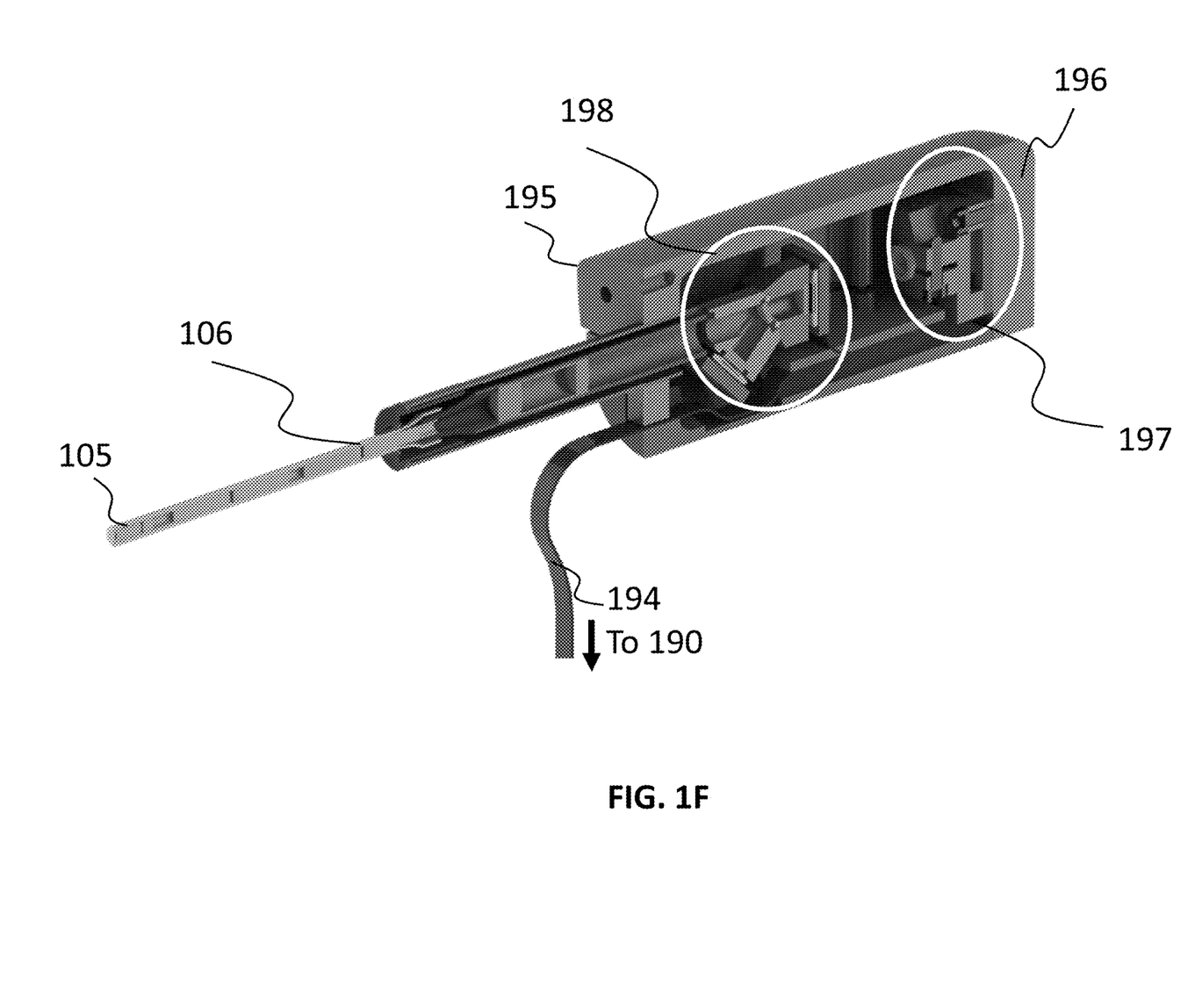
FIG. 1F depicts an example implementation of portions of the 3D scanner.

FIG. 1F depicts an example implementation of the 3D scanner 195 front-end, in accordance with some example implementations. The 3D scanner 195 may have a shroud 196 that houses an illumination component 197 and a sensing component 198. A cable 194 can connect the 3D scanner to the processor 190. Connected to the shroud 196 of the 3D scanner is the scanner element 105, or probe, which includes lenses 106 to focus light. The illumination component 197 produces light that excites the fluorescent material in the inflatable membrane, as well as light that may allow for general viewing of the cavity being scanned and the area around the cavity, such as when locating an area of interest. The light generated by the illumination component 197 for general viewing may be white light generated by one or more light source, such as one or more light emitting diodes. The light generated by the illumination components 197 for excitation of the fluorescent material in the inflatable membrane may be blue light generated by one or more light source, such as one or more light emitting diodes. The sensing component 198 may include one or more of a mirror, a beam-splitter, a filter, and multiple detectors. Each detector sends data to the processor 190 through the cable 194. The data from the one or more detector may be combined, multiplexed, or otherwise processed before it is sent through the cable 194. The processor 190 may send commands, such as illumination, scanning, or focusing instructions, to the front-end of the 3D scanner through the cable 194. The configuration the components of the front-end of the 3D scanner shown in FIG. 1F is a representative configuration. The 3D scanner may have an illumination component 197, sensing component 198, probe 105, and processor 190 in other configurations suitable for scanning a cavity, such as an anatomical cavity.

Referring again to FIG. 1D, to determine distance from the scanner element 105 and a corresponding surface of the interior of membrane 110, the ratio of the intensity of two or more wavelengths or ranges of wavelengths may be used. Specifically, the intensity of the light emitted by the fluorescent material may be measured and recorded for at least two wavelengths, $\lambda_1$, $\lambda 2$, or ranges of wavelengths, one of which is the wavelength, or wavelength range, that is preferentially absorbed by the absorbing medium. The ratio of the intensity of two or more wavelengths, or ranges of wavelengths, at least one of which is preferentially absorbed by the absorbing medium, allows the 3D scanner 195 and/or processor 190 to calculate the distance between the fluorescent material of the inflatable membrane 110 and the distal tip of the scanner element 105 that receives the light 125, 130 from the fluorescent material. The light 115 from the scanner element 105 may scan the inner surface of the membrane 110 by illuminating points or areas on the inflatable membrane 110 in a sequential manner, so that an array of ratios of intensities of the wavelengths, and thus distances, corresponding to points on the inflatable membrane 110 can be created. As noted above, the scanner element 105 may move within the membrane 110 to allow illuminating portions along some, if not all, of the entire inner surface of the membrane 110.

The 3D scanner 195 may include a spectrometer to measure intensities for the two or more wavelengths, or ranges of wavelengths, of light from the fluorescent material. The wavelengths of light that can be compared include red light (such as light with wavelength ranging from about 620 to about 750 nanometers (nm)) and green light (such as light with wavelength ranging from about 495 to about 570 nm). Additionally, or alternatively, the intensity of other wavelengths of light can be measured and compared, such as any combination of violet light (approximately 380 to 450 nm), blue light (approximately 450 to 495 nm), green light (approximately 495 to 570 nm), yellow light (approximately 570 to 590 nm), orange light (approximately 590 to 620 nm), and red light (620-750 nm). The spectrometer can include one or more detectors, such as CCD (charge coupled device) or CMOS (complementary metal-oxide semiconductor) detectors, to measure the intensity of light, as well as implements to select the wavelengths to be measured, such as one or more grating, beam splitter, or filter.

The 3D scanner 195 may also measure the intensity of one or more wavelengths or ranges of wavelengths of light from fluorescent material embedded in, or on, the inflatable membrane as a function of the degree of inflation of the membrane. That is to say, the inflatable membrane can be inflated to multiple levels of inflation while inside of an anatomical cavity, and measurements of the intensity of one or more wavelengths or ranges of wavelengths of light emitted from fluorescent material embedded in or on the inflatable membrane can be recorded and used to determine at least a 3D image or a surface topography of the anatomical cavity corresponding to this one or more levels of inflation. In the case of the human ear, particularly the aural canal, the size of the canal and compliance of the tissue in the canal can be determined, and the location of anatomical features, such as the bone-cartilage junction, can be found. Knowledge of the shape, compliance, and location of anatomical features can be used to create a device that provides better sound transmission, more comfort to a device user, or for the development of device materials. In some example implementations, the membrane 110 may be dynamically inflated to different pressures to enable the 3D scanner 195 to better scan certain anatomical features, such as the bone-cartilage junction and the like. This may be aided by asking the patient to move her anatomical features, for example by chewing, during the scan, and by observing changes in measurements as a function of this anatomical feature displacement. In this way, an ear piece, hearing protection, or hearing aid may be made that provides better sound transmission, sound protection, or comfort to a wearer.

The 3D scanner 195 may, as noted above, excite points or portions of the inflatable membrane in a sequential manner to obtain data that allows for the determination of the shape and mechanical properties, such as compliance, of the anatomical cavity surrounding the inflatable membrane. These properties can also be determined statically or dynamically as a function of time. The scan method and path, or sequence of points selected by the user or the system, can be chosen to improve accuracy, speed, or repeatability of the measurements made by the system. For example, 3D scanner 195 including the scanning elements 105 may be configured to allow scanning in a variety of methods and patterns to obtain as accurate a rendering of the anatomical cavity as possible. Such methods and scan patterns may include a hub-and-spoke pattern, a spiral pattern, a left versus right cue pattern, and/or any other method or pattern.

In the case of scanner element 105, fluorescent imaging through medium 120 may, as noted, selectively absorb one wavelength, or range of wavelengths, of light over another, and this selective absorption may be used to determine depth from scanner element 105 to the fluorescent membrane 110. This depth measurement may, as noted, be based on a ratio of the absorbed-to-transmitted wavelengths or ranges of wavelengths of light. Moreover, a processor may correlate the depth measurement to the corresponding scan data/images. For example, a portion of the 2D scanner image of the fluorescent membrane 110 may be correlated to a depth measurement determined from the ratio of the absorbed-to-transmitted wavelengths of light. In this way, the 2D scanner data/image is processed into a 3D image or surface.

The inflatable membrane 110 can be created or selected to provide more accurate data. More accurate data can be generated by the 3D scanner when the fluorescent material of the inflatable membrane 110 and the medium 120 are selected to optimize the contrast between the intensities of at least two ranges of wavelengths of fluoresced light. A membrane 110 that minimizes reflected light from the anatomical cavity can also increase data accuracy when using light create 3D renderings of anatomical cavities. Other membrane characteristics that can improve the performance of the 3D scanning system, and thus the accuracy of the data, can include one or more of the following: the ability of the membrane to repeatedly inflate and conform to an anatomical cavity; the ability of the membrane to inflate without causing pressure or pain in the anatomical cavity during the scanning process; the reduction of noise due to light scattered or reflected (as opposed to fluoresced) by the fluorescent material in the membrane; the ability of the membrane to have features present that facilitate stitching together data from multiple scan areas; the ability of the membrane to be unaltered by exposure to the absorbing medium; the ability of the membrane to be unaltered by exposure to illumination during scanning; the reduction of noise by the membrane being opaque to ambient light or light from the surrounding cavity; the ability of the membrane material to prevent dye from leaching into the medium or surrounding environment; the ability to maintain accuracy by preventing the medium from permeating out of the inflatable membrane; life-time reproducibility of the data over time, temperature (in manufacturing, storage and/or shipping), and multiple uses; and/or other physical, opacity, and fluorescence characteristics.

The following provides a description of an example inflatable membrane implementation, and, in particular, performance criteria and use scenarios for the inflatable membrane; materials which make up the inflatable membrane in relation to the performance criteria and use scenarios; and ways to making the inflatable membrane.

Use of the Inflatable Membrane in 3D Scanning

As shown in FIG. 1E, when creating a 3D rendering of an anatomical cavity, the inflatable membrane 110 is substantially full of medium 120. Depending on some of the materials properties of the inflatable membrane 110, the shape of the membrane, and its insertion level into the cavity, the degree of inflation (e.g., the pressure applied), the inflatable membrane 110 substantially conforms to the shape of the anatomical cavity 182. The scanner element 105 can direct light 115 that impinges the inflatable membrane 110, and excites fluorescent material in or on the membrane to emit light 125, 130, with at least two distinct wavelengths, $\lambda_1, \lambda_2$, or ranges of wavelengths. As described above, the 3D scanner 195 can create a 3D rendering of the anatomical cavity, it can calculate certain mechanical properties of the anatomical cavity 182 when the inflatable membrane 110 is inflated to multiple pre-set pressures and scanned at each pressure, and the 3D scanner can approximate the location of anatomical features, such as those that exhibit a change in modulus of in the tissue of the anatomical cavity wall.

To accommodate these use modes, the inflatable membrane 110 can have certain characteristics. In some implementations, the inflatable membrane contains a fluorescent material, such as a dye or pigment, that returns an image of fluoresced light when illuminated with visible blue or UV (ultra-violet) light. In other implementations, the inflatable membrane contains a fluorescent dye that returns an image when illuminated with white light. Some implementations include an inflatable membrane that contains a fluorescent dye that returns an image when illuminated with light that is not visible to the naked eye, that is to say light has a wavelength that is outside the range of about 390 to 700 nm. In implementations where the inflatable membrane contains a fluorescent material that returns an image of fluoresced light when illuminated with visible blue light, the membrane can fluoresce red and green light. Alternatively, the membrane can fluoresce in any combination of two or more wavelengths, or ranges of wavelengths, of light in response to illumination with blue or white light. In such implementations, there may be a wavelength, band of wavelengths, multiple wavelengths, or multiple bands of wavelengths of illuminating light, such that the spectrum of the fluoresced light emitted in response to the illuminating light may not change by more than about 0.5% over the length of the inflatable membrane. For example, if the inflatable membrane fluoresces red and green light in response to illumination with visible blue light, the ratio of red to green fluoresced light may not vary by more than about 0.5% over the length of the membrane, more than 1.0%, or more than 2.0% over the length of the membrane. In implementations where the inflatable membrane fluoresces red and green light, the absorbing medium can be a red fluid that preferentially absorbs the green light.

An experimenter or membrane fabricator can test the inflatable membrane for the fluoresced light emitted without the absorbing medium in the system. In such tests, the ratio of intensities of a first wavelength, or range of wavelengths, of light to a second wavelength, or range of wavelengths, of light can be between a range of values, such as about 0.70 to about 0.75. The range for the values of the ratio of intensities of light may depend on the materials in the inflatable membrane, the medium used to inflate the membrane, the fluorescent dye, the illuminating optics of the 3D scanning system, and the detecting optics of the system. For example, if the inflatable membrane includes the fluorescent material Keystone Keyfluor Invisible Yellow, described in greater detail below, and fluoresces red and green light in response to illumination with visible blue light, the ratio of red to green fluoresced light can be between about 0.72 and about 0.74, such as about 0.73 to about 0.74.

Further, to verify the opacity of the inflatable membrane, tests can be done by an experimenter to measure the contribution of a background, such as the ear canal, to the noise in the fluorescence signal as the inflatable membrane is stretched a known quantity. For example, if the inflatable membrane fluoresces red and green light in response to illumination with visible blue light, the experimenter initially tests for the ratio of red to green fluoresced light when the membrane is not stretched. The experimenter then stretches, or strains, the inflatable membrane a known quantity, such as 50%, while the membrane sits over a background that is half black and half red. The experimenter can use a 3D scanning system without absorbing medium or a similar set-up to measure the ratio of fluoresced red and green light. Next, the experimenter can stretch the inflatable membrane to greater degrees, such as 100% beyond its original dimension, 150%, 200%, and so forth, while measuring the ratio of intensities of the two wavelengths of fluoresced light. When the change in the ratio of intensities of the two wavelengths of fluoresced light increases more for measurements taken over one portion of the background than the other, then the inflatable membrane is considered transparent to the wavelengths, or range of wavelengths, of fluoresced light. Conversely, when the change in the ratio of intensities of the two wavelengths of fluoresced light increases a similar amount for measurements taken no matter which portion of the background the membrane covered, then inflatable membrane is considered opaque to the wavelengths, or range of wavelengths, of fluoresced light.

Figure 2A:
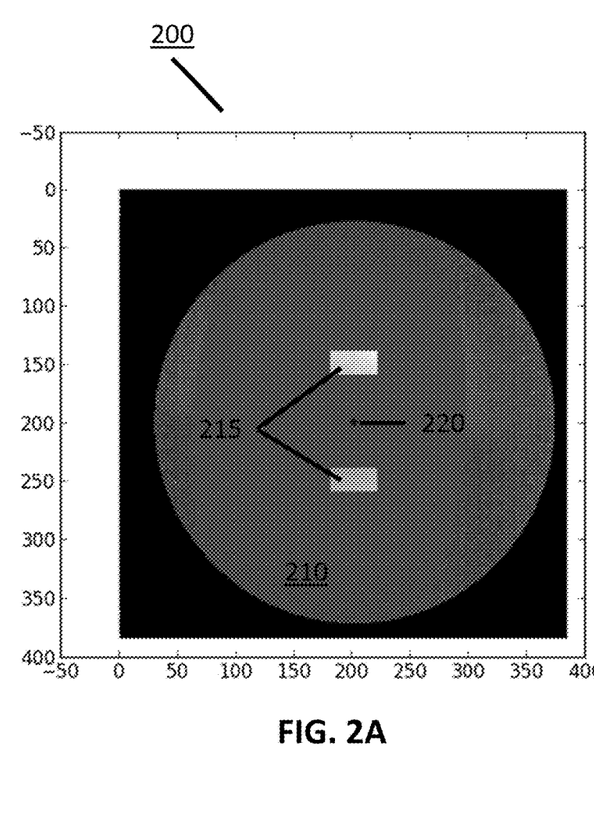
FIG. 2A shows a schematic of an experimental set-up for determining opacity of an inflatable membrane.
Figure 2B:
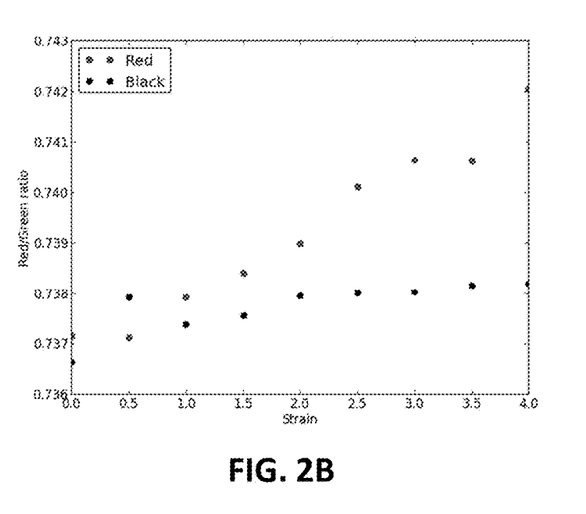
FIG. 2B shows representative data taken from an experimental set-up as in FIG. 2A, in which the inflatable membrane was not opaque, but partially transparent.
Figure 2C:
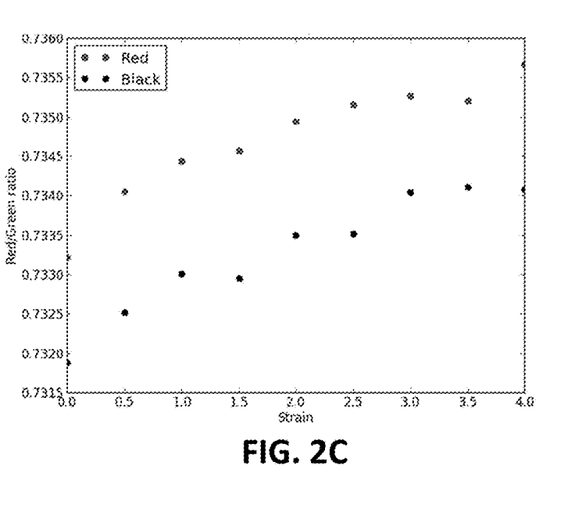
FIG. 2C shows data representative taken from an experimental set-up as in FIG. 2A, in which the inflatable membrane was substantially opaque.

FIG. 2A shows a representative image 200 of a portion of an inflatable membrane 210 placed in a test set-up by an experimenter. In this case, the membrane fluoresces red and green light when illuminated with visible blue light, and the background is half red, half black. The test set-up 200 includes a grid and a marking indicating a point 220 that corresponds to the principle point of a sensor in the sensing component (198 in FIG. 1F), as well as markings 215 equidistant from the principle point 220. FIG. 2B shows representative intensity data taken by an experimenter from an inflatable membrane that was not opaque, that is to say that the membrane was transparent. The data trends for the ratio of intensities of fluoresced light measured over the red and black portions of the background do not follow similar trends, and in fact, the data cross when the strain applied was 1.0. This difference in slope of the data from the red portion of the background and the data from the black portion indicates that the background contributed noise to the intensities measured, and thus the membrane allowed some of the light to be contributed by (e.g., reflected or fluoresced) from the background and measured as fluoresced red light, coming from the inflatable membrane. In contrast, FIG. 2C shows representative intensity data taken by an experimenter from an inflatable membrane that was opaque. The data taken by the experimenter can be seen to follow the same slope over many strains, and thus thicknesses, of the inflatable membrane. This type of data indicates that the background did not contribute appreciable amounts of light to the light that was measured as fluoresced light, and thus the inflatable membrane tested in FIG. 2C was opaque over the range of strains tested. The strain range tested correlates to the strain in the inflatable membrane expected during scanning an anatomical cavity.

To ensure that the inflatable membrane is sufficiently robust and compliant, the inflatable membrane may have one or more of the following physical characteristics. First, the elastic modulus of the inflatable membrane may range from about 40 kPa to 100 kPa, such as from about 50 kPa to 100 KPa, including from about 60 kPa to about 95 kPa under strain ranging from 100% to 400%. Second, the engineering strain at break under tension for representative samples of the inflatable membrane material may range from about 6 to 10, such as from about 7 to 10, including from about 7 to 9. Third, after cyclic strain six times to 3 (i.e. 300%), the inflatable membrane may not permanently deform more than about 11%.

Additionally, the inflatable membrane may maintain full functionality when exposed to temperatures ranging from about 18° C. to 30° C. for any length of time to ensure its compatibility with multiple use scenarios. In some implementations, the temperature range over which the inflatable membrane can maintain full functionality for any length of time may be about 15° C. to 40° C., 18° C. to 37° C., 18° C. to 35° C., 18° C. to 30° C., or 20° C. to 30° C. Further, the inflatable membrane may maintain full functionality when exposed to ambient operating relative humidity ranging from about 5% to 85%. In some implementations, the ambient operating relative humidity in which the inflatable membrane may maintain full functionality may range from about 5% to 90%, such as about 10% to 85%, including about 10% to 80% relative humidity.

The inflatable membrane may also have characteristics that ensure it is robust enough for shipping and storage. In some implementations, the inflatable membrane may maintain full functionality following exposure to temperatures ranging from −29° C. to 60° C. for up to 24 hours. The inflatable membrane may withstand exposure, during shipping, of a maximum altitude of 2,400 meters for up to 24 hours in some implementations. Additionally, the inflatable membrane may have a three-year shelf life when stored at a temperature from about 18° C. to 28° C. at an altitude of about 0 to 10,000 feet (about 0 to 3.048 kilometers).

Full functionality may indicate that the inflatable membrane is sufficiently robust (e.g., tear-resistant, impervious to the absorbing medium), sufficiently compliant (e.g., soft enough to conform to the cavity being scanned), sufficiently opaque, and/or sufficiently fluorescent in response to illumination over the range of conditions described. Full functionality may also encompass retention of other qualities, described in greater detail above, that allow for accurate and repeatable data collection during 3D scans.

The inflatable membrane 110 of the 3D scanning system may also be used multiple times. In some implementations, the inflatable membrane is intended for at least 4 uses. In such implementations, the ability of the inflatable membrane to resist appreciable permanent deformation after one, or after two, or even three uses may be necessary. This includes the ability of the inflatable membrane to resist appreciable permanent deformation after cycling through a series of inflation pressures two, three, four, or more times. Additionally, the inflatable membrane may be able to maintain uniformity of fluorescence and opacity after multiple inflations, and even after multiple cycles of inflation pressures with each inflation iteration. For inflatable membranes that are intended for multiple inflation use, the materials properties, such as yield stress, elastic modulus, and the like, as well as the optical characteristics of opacity and fluorescence may perform within a predetermined percentage of the initial values over all of the inflations. For example, the mechanical materials properties and the optical materials properties may not degrade more than 2% over four inflations, or they may not degrade more than 3%, more than 4%, or the materials properties may not degrade more than 5% over four inflations.

Materials of the Inflatable Membrane

The inflatable membrane may include a matrix material, pigment for opacity, and fluorescent material, such as pigment or dye. All of the materials individually are selected to be biocompatible and to illicit as little reaction from the human body as possible. This may be considered important because a goal of using the inflatable membrane with 3D scanning system is to improve comfort for the patient during fabrication of a 3D rendering or model of his or her anatomical cavity. The matrix material may be a biocompatible or bio-inert polymer or mixture of polymers. The pigment for opacity may be tested or accepted by a regulatory agency to have little cytotoxic activity at the particle sizes and exposure levels that are possible when using the inflatable membrane. Similarly, the fluorescent material may be accepted by the scientific community and/or regulatory entities as being acceptable for use in contact with skin and the lining of other anatomical cavities.

The inflatable membrane may comprise predominantly the matrix material. Correspondingly, the raw materials of the inflatable membrane may comprise predominantly the matrix material or its precursors, as well. The matrix material may be combined as a liquid with the pigment for opacity and fluorescent dye during fabrication. Post-mixing curing, which can include casting, molding, heating, or the addition of further chemicals, may cause the matrix material to transition from a pourable, or spreadable material, to a solid material with sufficient elasticity and toughness, as described above, to be useful in the scenarios described herein, such as multiple inflations at multiple degrees of inflation (e.g., multiple degrees of pressurization of the inflatable membrane).

Figure 3:
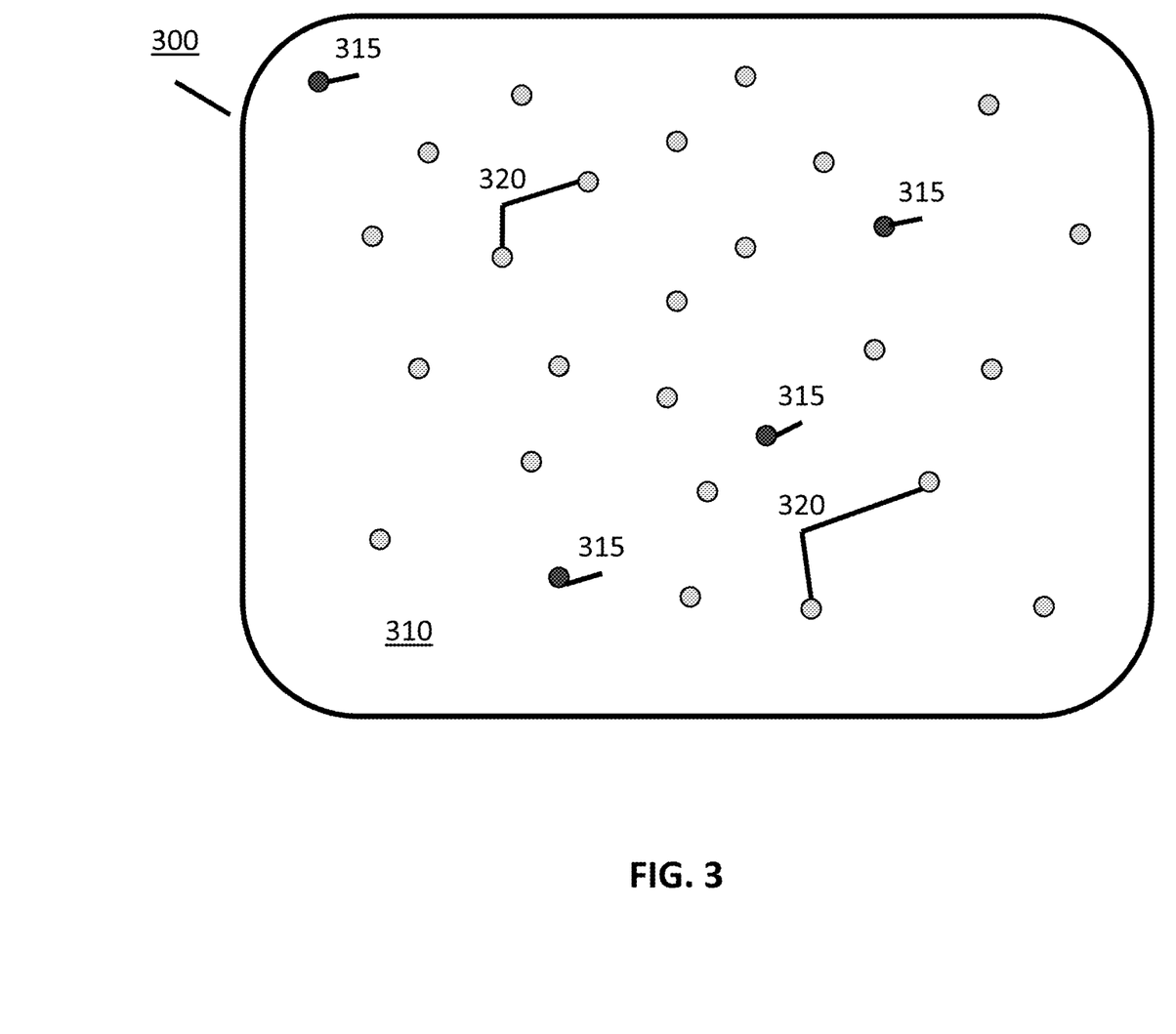
FIG. 3. is a schematic of a magnified, representative portion of an inflatable membrane.

FIG. 3 shows a schematic of a portion of a representative inflatable membrane 300, enlarged many times. The inflatable membrane 300 has a matrix material 310 with pigment particles 315 for opacity and particles of fluorescent material 320 which are not distinguishable to the naked eye as discrete particles when in the inflatable membrane. The inflatable membrane 300 has the pigment particles 315 and fluorescent material 320 embedded in the bulk of the matrix material 310, on the surface of the inflatable membrane, or some combination thereof. For example, the pigment particles 315 may be embedded within the matrix material 310 and the fluorescent material 320 may be on the surface of the inflatable membrane 300, or the fluorescent material 320 may be embedded in the matrix material 310 and the pigment particles 315 may be on the surface of the inflatable membrane 300. Alternatively, the matrix material 310 may have both the pigment particles 315 and the fluorescent material 320 embedded in it and additional fluorescent material may be applied to the surface of the inflatable membrane, such as fiducials or other markers. The materials properties of the inflatable membrane 300 may be attributable to the combination of the matrix material with the pigment and the fluorescent material.

The matrix material may include one or more polymer. The matrix material may be a low-hardness (e.g., a low-durometer) liquid silicone rubber, a liquid silicone elastomer, or a combination thereof. Exemplary silicones include NuSil® Silicone MED-4901, NuSil® Silicone MED-4905, NuSil® 4286, Elastosil® 7600, Elastosil® 7671, Silpuran® 2400, Bluestar 4301, 7684-40, 2420-30, and any of the aforementioned silicones with the amount (e.g., mass) of silica used in production of the silicone reduced by a predetermined amount, such as 1%, 2%, 5%, 10%, 20%, and/or other amounts as well. In some implementations, more of one of the components of the matrix material may be used to modify the cross-linking density of the matrix material, reducing the silica concentration. The matrix material of the inflatable membrane can also include silica enriched silicone, latex, polyurethane, polyisoprene, engineered thermoplastic polyurethane, thermoplastic polyethylene, plastisols, or any combination thereof. One or more thermoplastic elastomers may also be included in the matrix material, such as the thermoplastic elastomer by TeknorApex®, MD-447.

The pigment for opacity may include any suitable biocompatible particulates, including suitable metals, metal oxides, metal carbides, and carbon blacks. In some implementations, the pigment for opacity is a carbon black, such as a channel carbon black, a furnace carbon black, a lampblack, a thermal carbon black, an acetylene carbon black, or any combination thereof. The pigment can include primary particles, aggregates of primary particles, and agglomerates of primary particles. The primary particles can range in diameter from about 15 nm to about 20 nm. The aggregates can range in diameter from about 50 nm to about 400 nm. Agglomerates of the primary particles can range in diameter from the size of aggregates up to 2 mm. In some implementations, the primary particle size of the pigment can range from about 10 to 30 nm, the size of aggregates of primary particles of pigment can range from about 50 to 200 nm, and aggregates of pigment can be up to 2 mm in diameter. Further, some exemplary implementations of a pigment for opacity include high-purity furnace carbon black that has been approved by the Federal Drug Administration of the United States of America as suitable for use in cooking applications, such as pots and pans. Such high-purity furnace carbon black can have total polynuclear aromatic hydrocarbons (PAHs) at a level not exceeding about 0.5 parts per million (ppm) and benzo[a]pyrene not exceeding about 5.0 parts per billion (ppb).

The fluorescent material of the inflatable membrane may be of a single type of fluorescent dye or a combination of fluorescent dyes. Any fluorescent material, such as dye or pigment, or combination of fluorescent material with a large Stoke's shift and a broad emission spectrum with at least two bandwidths that are suitable to use as signal in the 3D scanning system can be used in the inflatable membrane. In some implementations, the fluorescent material of an inflatable membrane can be a fluorescent dye that has reduced or negligible reflectance at the wavelengths which a 3D scanning system uses as signal. In other implementations, the inflatable membrane contains a concentration of fluorescent material high enough to obtain good signal, but low enough for any reflection from the fluorescent material to be ignored. For example, for a 3D scanning system that measures the relative intensities of red and green light, the ideal fluorescent material may be a dye that absorbs at higher energy wavelengths, such as blue or UV; a dye that fluoresces light that includes red and green wavelengths; and a dye that is used at a concentration such that the dye reflects little to no red or green light. Such a dye may be considered transparent to the wavelengths of light selected by the system, or a user, as the signal wavelengths. In this case, a dye that is excited by blue light, fluoresces yellow light (that includes red and green light in its emission spectrum), and is transparent to red and green light is an ideal, invisible fluorescent dye. The dye is invisible in that it does not contribute substantially to the signal noise because it does not reflect, scatter, or otherwise perturb the fluoresced light at the wavelengths of interest, namely the red and green wavelengths. The dye may be invisible also if it is used at a concentration where any reflectance or scattering is negligible at the wavelengths of interest. One such exemplary dye in this scenario is commercially available as Keystone KeyfluorInvisible Yellow OB-549. This fluorescent dye may comprise a metal complex with a melting point of around 350-356° C., is excited by light with any light in a range from UV to blue, such as light with a wavelength of about 366 nm, and which has an emission spectra with a peak at a wavelength of 549 nm. The dye may be a yellow powder when not mixed with a matrix material and has a particle size distribution, based upon the particle diameter, ranging from about 2.0 microns to about 20 microns. The particles may be rod shaped (e.g., high aspect ratio particles) with a diameter of about 2 microns and a length of about 20 microns. An invisible, or transparent, fluorescent dye used as the fluorescent material in an inflatable membrane can be a metal complex, an organic molecule, or any other material with suitable excitation, emission (i.e., fluorescent), and reflective and scattering properties.

Fabrication of the Inflatable Membrane

The combining and processing of the raw materials of the inflatable membrane may correlate strongly to the physical and optical properties of the finished inflatable membrane used in the 3D scanning system. Fabrication methods that can be used to make inflatable membranes may be described below. Variation of the ratio of the constituent materials of the inflatable membrane may cause variation in the performance of the inflatable membrane, and such variations in raw materials will be described first. Then, various ways of mixing the raw materials will be described.

The raw materials for fabricating an inflatable membrane can include, a matrix material, a pigment for opacity, and a fluorescent material, as described above. The raw materials can be combined by weight in the following ratios, in which the first number in the ratio is the weight of the raw material (e.g., opaque pigment or fluorescent material) and the second number is the weight of the matrix material in the mixture. In some implementations, an inflatable membrane can include about 1:400 by weight of pigment for opacity and about 1:50 by weight of fluorescent material. Alternatively, an inflatable membrane can include pigment for opacity by weight in an amount ranging from about 1:350 to about 1:450 and fluorescent material by weight in an amount ranging from about 1:100 to about 1:25.

In some implementations, a mixture called a masterbatch, that is used to fabricate an inflatable membrane, can be created. The masterbatch mixture can be a small volume of material, such as about 10 g, that includes, for example, about 0.09±0.01 g of pigment for opacity, about 0.73±0.01 g of fluorescent dye, and about 9.17±0.02 g of matrix material. In other implementations, the masterbatch mixture can be a larger volume of material, such as about 240 g, that includes about 0.6±0.01 of pigment for opacity, about 4.8±0.01 g fluorescent dye, and about 120.0±0.02 g matrix material. In some such implementations, the matrix material is a two-part elastomer or polymer, and only one part is added to the masterbatch. In other implementations, the matrix material does not have more than one portion, and part of the mass of the matrix material is added to the masterbatch, and the rest of the matrix material is combined with the masterbatch following some processing.

Fabricating the masterbatch mixture can include some processing of the combined matrix material. Such processing can include mixing in speed mixer, milling in an attrition mill, ball milling, using media while milling, mixing, or centrifuging the mixture. The media can be ball milling media, such as ceramic or metal media. Ceramic media can include yttria stabilized zirconia pellets or balls, silica balls, alumina pellets or balls, or the like. Metal media can include stainless steel balls, aluminum balls, or metal balls of any metal or alloy that is corrosion resistant and wear resistant in the presence of the matrix material, pigment, and fluorescent material. Fabricating the masterbatch can also include allowing the mixture to rest, or reduce in temperature, after mixing to an elevated temperature. The rest time can vary, and can include a time of at least about 30 seconds, at least about 60 seconds, at least about 90 seconds, and at least about 120 seconds. During the rest time, the masterbatch mixture can be scraped down from the sides of the mixing container, as well as returning to ambient or near ambient temperature.

During fabrication of the masterbatch mixture, as well as the final mixture that is to become the inflatable membrane, a centrifuge set to various speeds of mixing can be used, with speeds ranging from about 1500 revolutions per minute (RPM) to about 3000 RPM, including from about 2000 RPM to about 2500 RPM. Also, various sizes of milling or mixing media can be used, of the material and shape described above, and the number of media can also be varied.

After the spreadable, final mixture that is to become the inflatable membrane is created, the mixture can be cured, molded, or dip-coated into sheets or other suitable shapes for the inflatable membrane. Curing the inflatable membrane can include casting the membrane onto metal sheets, such as aluminum sheets, heating the cast material, or simply aging the material, such as by allowing it to sit, for an extended period of time. Curing may also include compression molding, transfer compression molding, or injection molding, where any of these molding operations may use a single or multi-shot process.

Figure 4:
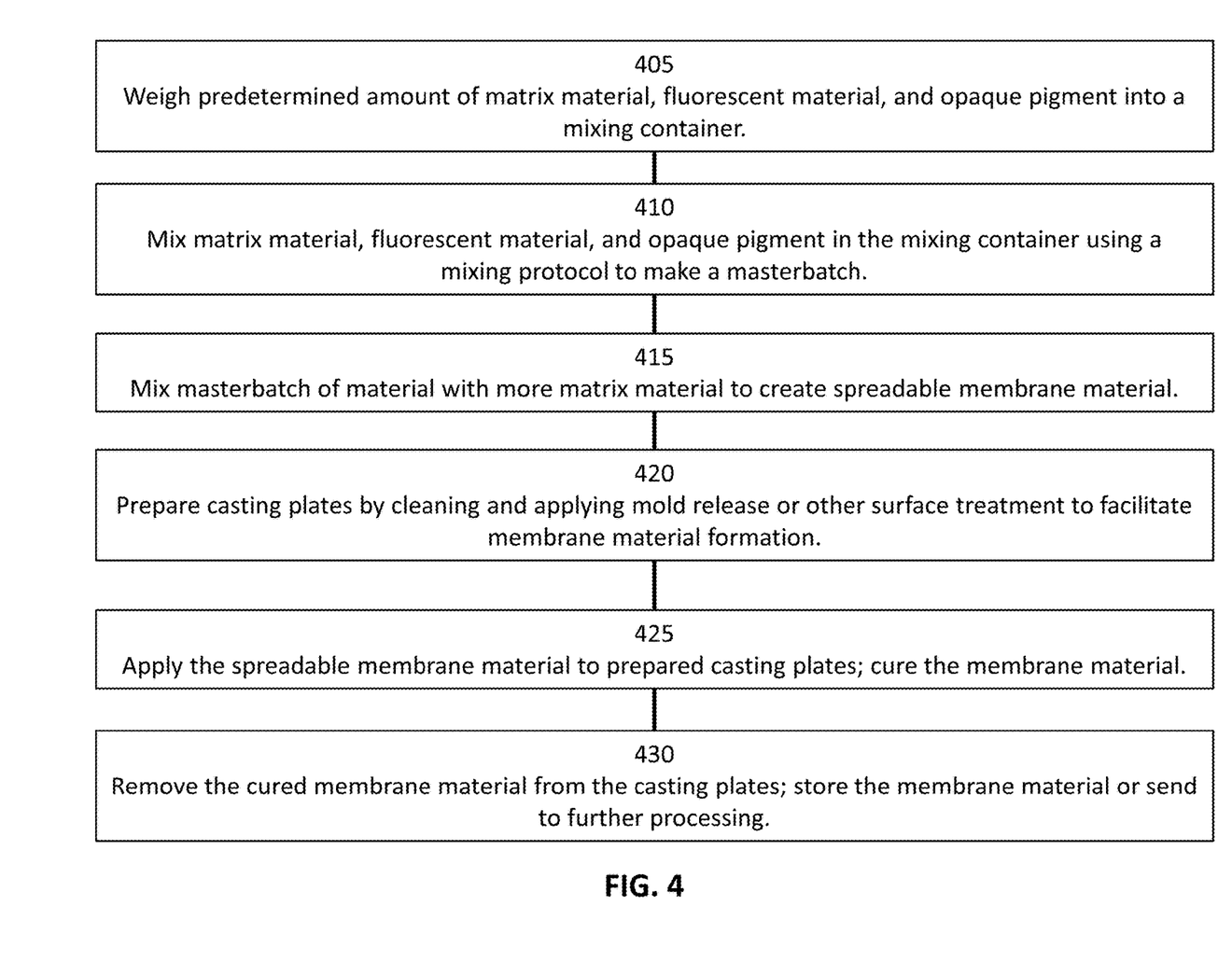
FIG. 4 a block diagram showing a representative method of making inflatable membrane material.

FIG. 4 is a block diagram with exemplary processes in producing an inflatable membrane material with the characteristics described herein. As the amount of the constituent materials may be important to the final materials characteristics, the first step is for an experimenter or membrane fabricator to carefully weigh out predetermined amounts of the matrix material, opaque pigment, and fluorescent dye into a mixing container, as in 405. The material weighed out typically is for the creation of a masterbatch mixture, and it is mixed accordingly, 410. The mixing protocol for creating a masterbatch can include using a centrifuge, such as a dual asymmetric centrifuge, to initially spin the material in the mixing container for a predetermined time at a predetermined speed, such as for about 60 seconds at 2500 revolutions per minute (RPM). The protocol can then specify for the experimenter or membrane fabricator to scrape the material down from the sides of the mixing container and to add mixing or milling media, such as about ten ceramic cylinders (e.g., 10 milimeter cylinders), and then to spin the material in the mixing container for a predetermined time at a predetermined speed, such as for about 60 seconds at about 2100 RPM. After mixing, the masterbatch mixture can be allowed to rest, or cool, for a predetermined amount of time, such as two minutes, then the experimenter or membrane fabricator can scrape down the sides of the mixing container and then repeat spinning the mixing container. An experimenter, or membrane fabricator, can do this repeated resting, scraping, and spinning a set number of times each process or until achieving a desired consistency. The experimenter or membrane fabricator can repeat the protocol to produce a masterbatch mixture, as needed, to create the volume or mass of material for the amount of inflatable membranes he or she wishes to make.

Once the masterbatch mixture is made, 410, more matrix material can be mixed with the masterbatch mixture by the experimenter or membrane fabricator to arrive at the final ratio of the constituent materials, 415. This can be about a 1:1 mixture of the masterbatch mixture and pure matrix material, or it can be a different ratio of masterbatch mixture to pure matrix material. In some implementations, the matrix material can have two components, one of which the experimenter or membrane fabricator mixes with the masterbatch mixture, while the other component is mixed in later to arrive at the final ratios of the constituents. In some implementations, the masterbatch and pure matrix material, or masterbatch and second component of the matrix material, are not mixed until right before the experimenter or membrane fabricator is ready to cast or cure the membrane. Alternatively, or additionally, the masterbatch and matrix material can be mixed using a mixing apparatus, such as centrifuge, as well as mixing or milling media to create a spreadable mixture that eventually becomes the inflatable membrane material, as in box 415.

In some implementations, casting plates are used to form and cure the inflatable membrane material. The experimenter or membrane fabricator prepares the casting plates, as in box 420. The casting plates can be ceramic, metal, polymer or any suitable combination thereof, and the experimenter or membrane manufacturer can clean the plates with soap and water, with organic solvents, with mild acid, or a combination thereof. After cleaning, the experimenter or membrane fabricator can treat the casting plates with a surface treatment, such as a mold release agent applied by the experimenter or membrane fabricator, as in 420. The experimenter or membrane fabricator can then pour the spreadable membrane material onto one of the casting plates, then he or she can place a second casting plate above the spreadable membrane material. Then the experimenter or membrane fabricator can cure the membrane material, box 425. Alternatively, the casting plates can be attached to an apparatus that allows for the simultaneous application of the casting plates and conveyance of the spreadable membrane material along a path. Such conveyance can also include the application of heat or other modifications to the environment, such as relative humidity, by a membrane curing or fabricating facility or system. The application of heat or adjustment of the environment can facilitate curing of the inflatable membrane material. Finally, the experimenter or membrane fabricator can remove the cured membrane material from the casting plates, and he or she can store the inflatable membrane material or send the membrane material to another facility for further processing. Further processing can include the application of more fluorescent material to create fiducial markings, cutting and joining the inflatable membrane material to create an inflatable membrane sized appropriately for an intended use, assembly into a system, and the like. Although the previous examples referred to specific times, sizes, ratios, speeds (e.g., RPM), other values may be implemented as well.

Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. In various example implementations, the methods (or processes) can be accomplished on mobile station/mobile device side or on the server side or in any shared way between server and user equipment/mobile device with actions being performed on both sides. The phrases "based on" and "based on at least" are used interchangeably herein. Other implementations may be within the scope of the following claims.

What is claimed:

1. An inflatable membrane configured to inflate within an anatomical cavity for use with a scanning system, the inflatable membrane comprising:
   a matrix material, wherein the matrix material forms 95.9% to 98.8% by weight of the inflatable membrane;
   a pigment for opacity, wherein the pigment for opacity forms at least 0.12% by weight of the inflatable membrane, and wherein the pigment for opacity is mixed into the matrix material; and
   a fluorescent material, wherein the fluorescent material fluoresces a first wavelength of light and a second wavelength of light, and wherein the fluorescent material forms 1.0% to 3.8% by weight of the inflatable membrane.

2. The inflatable membrane of claim 1, wherein the matrix material comprises a silicone.

3. The inflatable membrane of claim 1, wherein the pigment for opacity comprises a carbon black.

4. The inflatable membrane of claim 3, wherein the carbon black comprises furnace carbon black.

5. The inflatable membrane of claim 4, wherein the carbon black comprises high-purity carbon black.

6. The inflatable membrane of claim 4, wherein the carbon black comprises at least one of: total polynuclear aromatic hydrocarbons at a level not exceeding about 0.5 parts per million; and benzo[a]pyrene at a level not exceeding about 5.0 parts per billion (ppb).

7. The inflatable membrane of claim 3, wherein the carbon black comprises primary particles with diameters ranging from about 15 nm to about 20 nm, wherein the carbon black comprises aggregates, of the primary particles, with diameters ranging from about 50 nm to about 400 nm, and wherein the carbon black comprises agglomerates, of the primary particles, with diameters ranging from the diameters of the aggregates to about 2 mm.

8. The inflatable membrane of claim 1, wherein the fluorescent material is excitable by light with wavelengths ranging from ultra-violet to blue light.

9. The inflatable membrane of claim 1, wherein the fluorescent material has an emission spectra with a peak at a wavelength of about 549 nanometers.

10. The inflatable membrane of claim 1, wherein the fluorescent material comprises a fluorescent dye.

11. The inflatable membrane of claim 1, wherein the fluorescent material comprises a fluorescent pigment.

12. The inflatable membrane of claim 1, wherein the first and second wavelengths of light are ranges of wavelengths of light.

13. The inflatable membrane of claim 3, wherein the carbon black comprises primary particles with diameters ranging from about 10 nm to about 30 nm, wherein the carbon black comprises aggregates, of the primary particles, with diameters ranging from about 50 nm to about 200 nm, and wherein the carbon black comprises agglomerates, of the primary particles, with diameters ranging from the diameters of the aggregates to about 2 mm.

14. The inflatable membrane of claim 1, wherein the pigment for opacity forms 0.2% to 0.3% by weight of the inflatable membrane.

15. The inflatable membrane of claim 1, wherein the ratio of the first wavelength and the second wavelengths of light is used to determine a distance from a surface of the inflatable membrane to a scanner element coupled to the inflatable membrane.

16. The inflatable membrane of claim 1, wherein the fluorescent material comprises invisible yellow.

17. The inflatable membrane of claim 1, wherein the first wavelength of fluoresced light comprises red light, and wherein the second wavelength of fluoresced light comprises green light.

* * * * *